US008845496B2

(12) United States Patent
Arrasvuori et al.

(10) Patent No.: US 8,845,496 B2
(45) Date of Patent: Sep. 30, 2014

(54) SYSTEM AND METHOD FOR GAMING

(75) Inventors: Juha Arrasvuori, Tampere (FI); Jukka A. Holm, Tampere (FI); Antti Eronen, Tampere (FI); Timo Kosonen, Tampere (FI); Kai Havukainen, Lempaala (FI); Mikko Heikkinen, Tampere (FI)

(73) Assignee: Nokia Corporation, Espoo (FI)

(*) Notice: Subject to any disclaimer, the term of this patent is extended or adjusted under 35 U.S.C. 154(b) by 1312 days.

(21) Appl. No.: 11/394,019

(22) Filed: Mar. 29, 2006

(65) Prior Publication Data
US 2007/0239479 A1 Oct. 11, 2007

(51) Int. Cl.
*A63B 71/00* (2006.01)
*G06Q 50/22* (2012.01)
*G06Q 10/10* (2012.01)

(52) U.S. Cl.
CPC ............... *G06Q 10/10* (2013.01); *G06Q 50/22* (2013.01)
USPC .................................................. 482/9; 482/8

(58) Field of Classification Search
CPC ............ A63B 24/00; A63B 24/0003; A63B 24/0062; A63B 24/0084; A63B 24/0087; A63B 2024/00; A63B 2024/0003; A63B 2024/0062; A63B 2024/0087; A63B 2024/0096
USPC ........... 482/1, 3–9, 51, 57, 902; 434/247, 255
See application file for complete search history.

(56) References Cited

U.S. PATENT DOCUMENTS

| | | | |
|---|---|---|---|
| 4,984,805 A * | 1/1991 | Medlock | 273/248 |
| 5,213,555 A * | 5/1993 | Hood et al. | 482/57 |
| 5,240,417 A * | 8/1993 | Smithson et al. | 434/61 |
| 5,547,439 A * | 8/1996 | Rawls et al. | 482/5 |
| 6,152,856 A * | 11/2000 | Studor et al. | 482/8 |
| 6,450,922 B1 * | 9/2002 | Henderson et al. | 482/8 |
| 6,786,848 B2 * | 9/2004 | Yamashita et al. | 482/8 |
| 6,902,513 B1 * | 6/2005 | McClure | 482/8 |
| 2001/0001303 A1 * | 5/2001 | Ohsuga et al. | 482/5 |
| 2003/0078138 A1 * | 4/2003 | Toyama | 482/8 |
| 2006/0040793 A1 * | 2/2006 | Martens | 482/8 |
| 2006/0229163 A1 * | 10/2006 | Waters | 482/8 |
| 2007/0042868 A1 * | 2/2007 | Fisher et al. | 482/8 |
| 2008/0102424 A1 * | 5/2008 | Holljes | 434/247 |

* cited by examiner

*Primary Examiner* — Oren Ginsberg
(74) *Attorney, Agent, or Firm* — Diithavong & Steiner, P.C.

(57) ABSTRACT

Systems and methods applicable, for instance, in gaming. Functionality might, for instance, be provided wherein one or more users are, in the context of a video game, presented with one or more real-world fitness tasks to be performed. Various monitoring operations might, for example, be performed. Various compensatory operations might, for example, be performed. Such compensatory operations might, for instance, take into account user fitness levels and/or environments in which real-world fitness tasks are performed.

29 Claims, 5 Drawing Sheets

SYSTEM AND METHOD FOR GAMING

FIELD OF INVENTION

This invention relates to systems and methods for gaming.

BACKGROUND INFORMATION

In recent times, there has been an increase in the playing of video games. For example, many individuals have increasingly come to prefer playing video games (e.g., multiplayer video games) over other forms of entertainment, challenge, and/or interaction with others.

Accordingly, there may be interest in technologies applicable, for instance, to video games.

SUMMARY OF THE INVENTION

According to embodiments of the present invention, there are provided systems and methods applicable, for instance, in gaming.

For example, in various embodiments functionality might be provided wherein one or more users are, in the context of a video game, presented with one or more real-world fitness tasks to be performed. Various monitoring operations might, in various embodiments, be performed.

Various compensatory operations might, in various embodiments, be performed. Such compensatory operations might, for example, take into account user fitness levels and/or environments in which real-world fitness tasks are performed.

DETAILED DESCRIPTION OF THE INVENTION

General Operation

According to embodiments of the present invention, there are provided systems and methods applicable, for instance, in gaming.

For example, in various embodiments functionality might be provided wherein one or more users are, in the context of a video game (e.g., a multiplayer video game), presented with one or more real-world fitness tasks to be performed. Such real-world fitness tasks might, for instance, include running, swimming, climbing, and/or use of exercise equipment. Completion of a task might, in various embodiments, result in advancement in the game and/or in another real-world fitness task being presented.

Various monitoring operations might, in various embodiments, be performed. For example, various monitoring might be performed with respect to users performing real-world fitness tasks. As another example, various monitoring might be performed with respect to the one or more environments in which real-world fitness tasks are performed. In various embodiments, determination might be made as to whether or not real-world fitness tasks are acceptably performed (e.g., whether or not acceptable locations and/or acceptable equipment are employed).

Various compensatory operations might, in various embodiments, be performed. Such compensatory operations might, for example, take into account user fitness levels. As another example, such compensatory operations might take into account one or more environments in which real-world fitness tasks are performed. It is noted that, in various embodiments, fitness tests might be administered to users.

Various aspects of the present invention will now be discussed in greater detail.

Game Initiation and Game Play Operations

Figure 1:
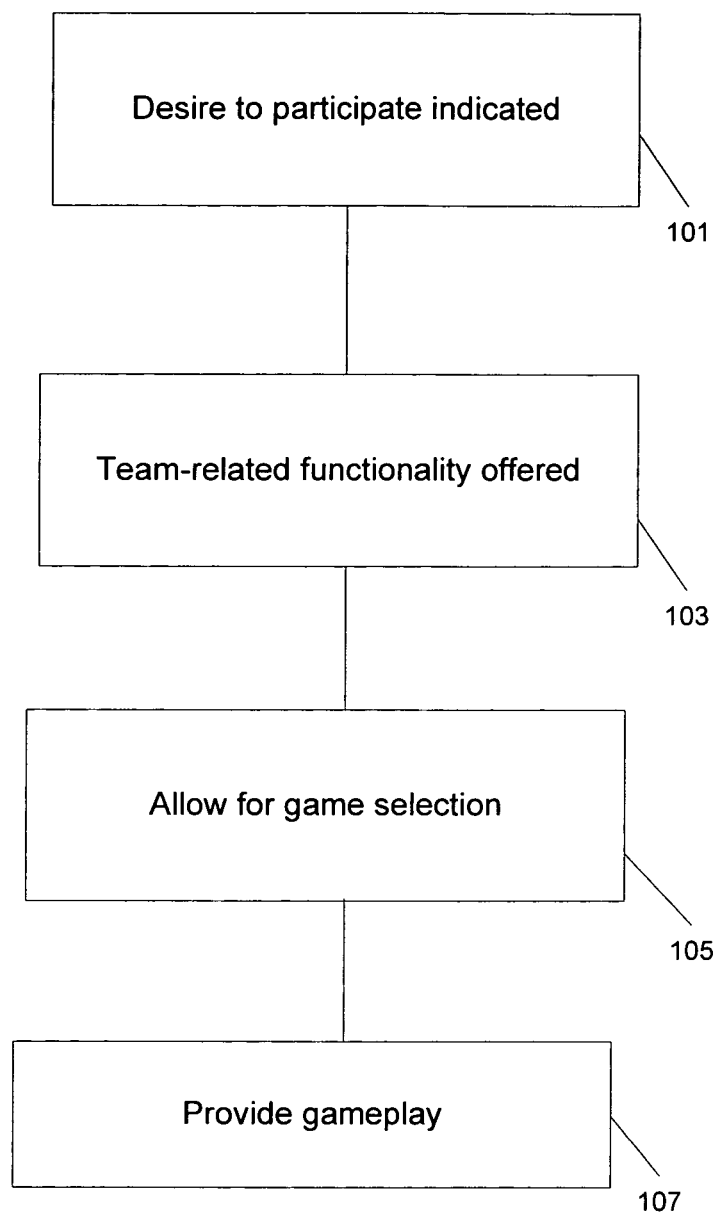
FIG. 1 shows exemplary steps involved in game initiation and game play operations according to various embodiments of the present invention.

With respect to FIG. 1 it is noted that, according to various embodiments of the present invention, a user wishing to participate in a video game might indicate a desire to do so via her wireless node and/or other computer (step 101). Such a video game might, for instance, be a multiplayer video game and/or a video game wherein one or more players perform real-world fitness tasks in the context of the game.

Various operations might, in various embodiments, be performed by the wireless node and/or other computer. For example, the wireless node and/or other computer might offer team-related functionality to the user (e.g., via a Graphical User Interface (GUI) and/or other interface) (step 103). The wireless node and/or other computer might, for instance, allow the user (e.g., via a GUI and/or other interface) to learn of available users, create one or more teams, to select one or more users for one or more new and/or existing teams, to invite one or more users to join one or more new and/or existing teams, to request to join one or more new and/or existing teams, and/or to accept invitation to join one or more new and/or existing teams. The user's wireless node and/or other computer might, in various embodiments, communicate with another wireless node and/or other computer. For example, the user's wireless node and/or other computer might act to perform a join operation with a server (e.g., a game server).

It is noted that, in various embodiments, team members might be located together and/or apart from one another. Accordingly, for instance, team members might be together in a single area and/or dispersed throughout the world. It is further noted that, in various embodiments, one or more wireless nodes and/or other computers (e.g., one or more wireless nodes and/or other computers of users, and/or one or more servers) might automatically form teams of users.

As another example of operations performed by the user's wireless node and/or other computer, the wireless node and/or or other computer might allow for selection of one or more games to play (step 105). Such functionality might be implemented in a number of ways. For example, the user might be able to select from one or more indicated games one or more games that she wished to play.

As another example, the user might receive indication of one or more games and be able to vote for one or more of the games as being ones that she wished to play. Such voting functionality might, for instance, be employed in the case where the user is a member of a team. Accordingly, for example, each team member might vote for one or more of one or more indicated games, and one or more games receiving the highest numbers of votes might be those that are selected for play by the team. Such indication, selection, and/or voting might, for instance, be via a GUI and/or other interface.

It is noted that, in various embodiments, the user's selection of one or more games might affect her membership in one or more teams. For instance, the user might select (e.g., via a GUI and/or other interface) one or more games as being ones that she wanted to play, and then (e.g., via a GUI and/or other interface) be informed that she has been made a member of, been offered membership in, and/or is able to request membership in one or more teams made up of, and/or to be made up of, other users wishing to play one or more of those games. It is noted that, in various embodiments, teams might not be employed.

As another example of operations performed by the user's wireless node and/or other computer, the wireless node and/or other computer might provide game play functionality to the user (step 107). Such functionality might be implemented in a number of ways.

For example, the user's wireless node and/or other computer might present (e.g., via a GUI and/or other interface) a game wherein the user is, within the context of the video game, presented with one or more real-world fitness tasks to be performed. Real-world fitness tasks might, for instance, include running, jogging, climbing, swimming, rowing, cycling, skiing, and/or using exercise equipment. Real-world fitness tasks might, for instance, be ones performable indoors and/or outdoors. It is noted that, in various embodiments, in the case where the game is a multiplayer game, other users playing the game might likewise be presented by their wireless nodes and/or other computers with one or more real-world fitness tasks to be performed.

As an illustrative example, the user's wireless node and/or other computer might present her with a medieval fantasy game. Such a game might, for instance, offer a number of stages that follow one another sequentially.

One stage of the game might, for instance, require that a landmark be reached in the game-world implemented by the video game. The user's wireless node and/or other computer might, for instance, indicate to the user that a real-world fitness task of jogging and/or running (e.g., running a specified distance) be performed by the user in order for the user (e.g., via an in-game character) to reach the landmark in the game-world.

Another stage of the game might, for instance, require that a mountain be scaled in the game-world. The user's wireless node and/or other computer might, for instance, indicate to the user that a real-world fitness task of climbing stairs (e.g., a specified number of stairs and/or a specified number of floors to ascend via stairs) be performed in order for the mountain to be scaled in the game-world. It is noted that, in various embodiments, the user might be able to employ either actual stairs (e.g., stairs in a building) and/or a stair machine, and/or might be instructed (e.g., by her wireless node and/or other computer) to use one and/or the other (e.g., the wireless node and/or other computer might instruct the user to use only a stair machine).

Yet another stage of the game might, for example, require that a river be crossed in the game-world. The user's wireless node and/or other computer might, for instance indicate to the user that the real-world fitness task of swimming and/or rowing (e.g., a specified distance) be performed in order for the river to be crossed in the game-world. It is noted that, in various embodiments, the user might be able to either row using a boat and/or a rowing machine, and/or might be instructed (e.g., by her wireless node and/or other computer) to use one and/or the other.

A further stage of the game might, for example, require that an enemy be defeated in the game-world (e.g., an enemy blocking the way of travel in the game-world). The user's wireless node and/or other computer might, for instance, indicate to the user that the real-world fitness task of performing one or more exercises and/or employing an exercise machine (e.g., a resistance machine) be performed in order to defeat the enemy in the game-world. Certain exercise details, certain numbers of repetitions, and/or one or more resistances to be employed might be specified with regard to the real-world fitness task. It is noted that, in various embodiments, one or more real-world fitness tasks might involve one or more users keeping their heart rates within one or more specified ranges. To illustrate by way of example, one or more users might be requested to keep their heart rates within one or more specified ranges while performing real-world fitness tasks involving running, swimming, climbing stairs, and/or using exercise equipment.

Successful completion of a real-world fitness task by the user might, in various embodiments, result in the user (e.g., via an in-game character) moving to a next stage of the game (e.g., a next stage with a corresponding real-world fitness task). It is noted that, in various embodiments, progression among game stages and/or corresponding real-world fitness tasks might be depicted. For example, an in-game character corresponding to the user and/or one or more in-game characters corresponding to other users (e.g., team members) might be (e.g., via a GUI and/or other interface) be depicted as, for instance, traveling from one point to another in the game-world.

It is noted that, according to various embodiments of the present invention, real-world fitness tasks might include tasks to be performed by only one user, tasks to be performed by more than one user (e.g., tasks to be performed by all users of a team, a specified number of users of a team, and/or specified users of a team), and/or tasks performable by either one user or by multiple users. To illustrate by way of example, a real-world fitness task of jogging and/or running that corresponds to a game stage of reaching a game-world landmark might be to be performed by all users of a team, a real-world fitness task of swimming and/or rowing that corresponds to a game stage of crossing a game-world river might be to be performed by all users of a team, and/or a real-world fitness task of performing one or more exercises and/or employing an exercise machine might be to be performed by only certain users of the team (e.g., by one user).

Such functionality might be implemented in a number of ways. For example, team members might be able to choose which one or more users should perform one or more particular real-world fitness tasks. Such choice might, for example, involve selection and/or voting by users (e.g., via their wireless nodes and/or other computers). Such voting might, for instance, be performed in a manner analogous to that discussed above. As another example, wireless nodes and/or other computers (e.g., one or more wireless nodes and/or other computers of users, and/or one or more servers) might decide which users are to perform particular real-world fitness tasks.

It is noted that, in various embodiments, there may be real-world fitness tasks that need to be successfully performed by all members of a team in order for the task to be deemed as having been completed by the team. Such might, for instance, be viewed as promoting healthy activity by inciting team members to encourage each other to successfully perform real-world fitness tasks. It is further noted that, in various embodiments, in the case where a real-world fitness task is performable by either one user or by multiple users, increasing the number of participant users might result in a higher score being awarded (e.g., to the team to which the users belong) for performance of the task. Such might, for instance, be viewed as promoting healthily activity by encouraging greater user participation in fitness tasks.

It is noted that, in various embodiments, users competing with and/or against one another might play at the same time and/or at different times. To illustrate by way of example, three users might play through a stage of a game having a corresponding real-world fitness tasks, with two of the users playing at the same time and the third of the players playing at a later or earlier time. It is further noted that, in various embodiments, a user's wireless node and/or other computer might (e.g., via a GUI and/or other interface) present her with a portal for viewing games available for play and/or users available as players and/or teammates.

As noted above, various real-world fitness tasks might involve compliance with a specified metric (e.g., a specified distance and/or a specified number of floors). Such a metric might, in various embodiments, be chosen by users. Such choice might, for instance, occur upon game initiation, prior to start of a game stage, and/or prior to start of a real-world fitness task attempt. Such choice by users might, for example, be implemented in a manner analogous to that discussed above (e.g., selection and/or voting might be employed). It is noted that, in various embodiments, a real world-fitness task might be considered to be over in the case where all participating users have met such a specified metric (e.g., in the case where all users have traveled a specified distance). Participating users might, in various embodiments, be informed (e.g., via GUIs and/or other interfaces of their wireless node and/or other computers) that a real-world fitness task is considered to be over.

It is noted that, in various embodiments, users might be presented with real-world fitness tasks in the context of a game-world athletic competition. For example, users might be able to participate in a game-world triathlon competition involving real-world fitness tasks of swimming, running, and cycling. Users might, in various embodiments, be able to select (e.g., via GUIs and/or other interfaces provided by their wireless nodes) the order in which they performed the fitness tasks. To illustrate by way of example, some users might choose to do the swimming task first while other uses might choose to do the cycling task first. Users might, for example, be able to indicate (e.g., via button press and/or via GUIs and/or other interfaces provided by their wireless nodes) moving from one fitness task to another. Information regarding such indication might, in various embodiments, be communicated among wireless nodes and/or other computers. For example, such information regarding such an indication might be communicated from a user's wireless node and/or other computer to a server.

In various embodiments, various of the above-discussed game initiation and game play operations might involve communication among one or more wireless nodes and/or other computers of users, and/or other wireless nodes and/or other computers (e.g., one or more servers). Such communication might, for instance, involve Remote Method Invocation (RMI), Java Messaging Service (JMS), Simple Object Access Protocol (SOAP), Object Exchange (OBEX) Object Push Profile (OPP), email, Multimedia Messaging Service (MMS), Short Message Service (SMS), Universal Mobile Telecommunications Service (UMTS), General Packet Radio Service (GPRS), Bluetooth, wireless local area network (e.g., WiFi (Wireless Fidelity)), Ultra Wide Band (UWB), IrDA (Infrared Data Association), wired network (e.g., Ethernet), and/or the Internet. Such WiFi might, for instance, be IEEE 802.11b and/or IEEE 802.11g. In various embodiments, servers might be operated by service providers, and/or one or more user wireless nodes and/or other computers might act as servers.

Monitoring and Feedback Operations

Monitoring corresponding to performance of real-world fitness tasks might, in various embodiments, be performed. Monitoring might, for instance, relate to users performing real-world fitness tasks and/or to one or to more environments in which real-world fitness tasks are performed. Monitoring might, for example, be performed by one or more wireless nodes and/or other computers (e.g., servers, and/or wireless nodes and/or other computers of users). It is noted that, in various embodiments, monitoring might involve communication among multiple wireless nodes and/or other computers (e.g., between a user wireless node and/or other computer and a server). Such functionality might be implemented in a number of ways.

Figure 2:
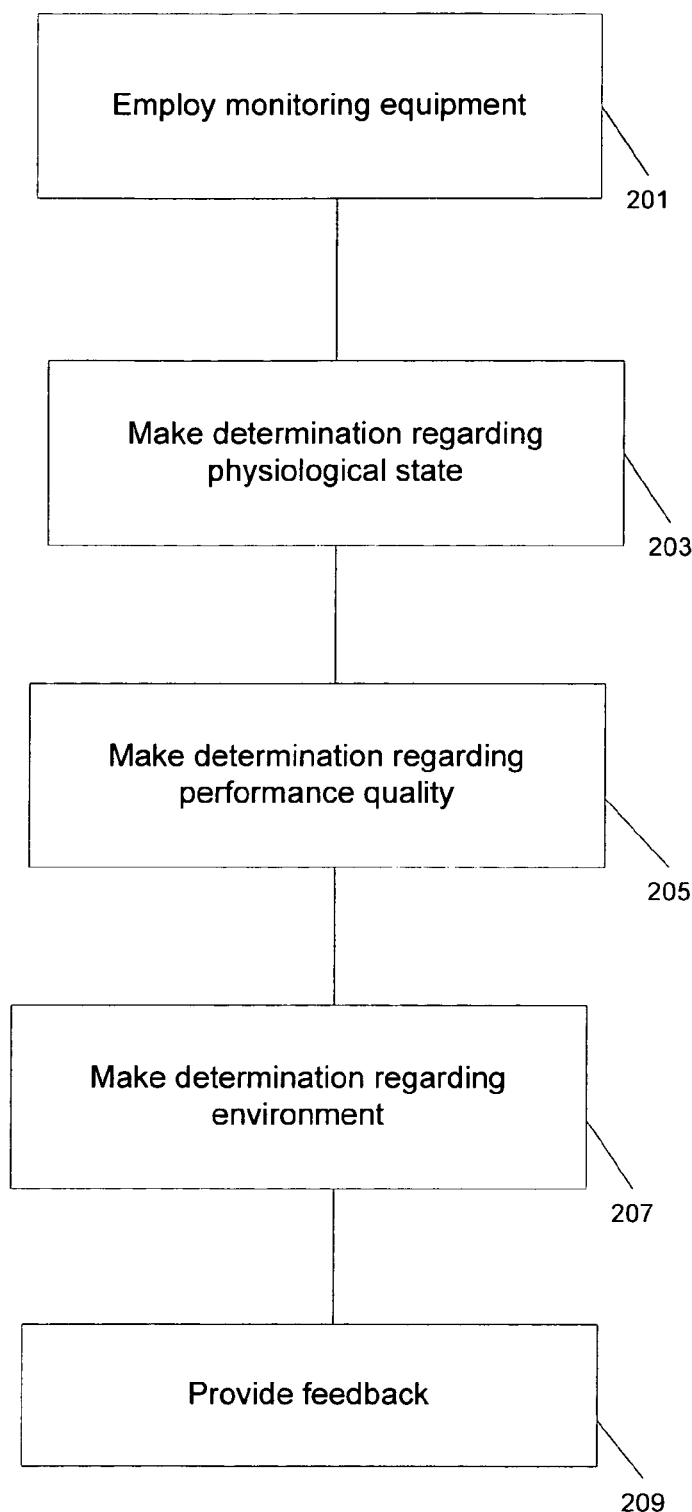
FIG. 2 shows exemplary steps involved in monitoring and feedback operations according to various embodiments of the present invention.

With respect to FIG. 2 it is noted that, for example, in various embodiments various monitoring equipment might be employed (e.g., by user wireless nodes and/or other computers) (step 201). Such monitoring equipment might, for instance, be integrated into and/or in communication with wireless nodes and/or other computers of users, and/or be attached to bodies of users. Users might, in various embodiments, wear their wireless nodes and/or other computers. Communication between monitoring equipment and a user's wireless node and/or other computer might, for instance, employ wired and/or wireless (e.g., via Bluetooth and/or WiFi) connection.

Employed monitoring equipment might, for instance, include equipment employable in monitoring and/or ascertaining geographical location (e.g., Global Positioning System (GPS) hardware might be employed), proximity (e.g., Radio Frequency Identification (RFID) tag interface hardware might be employed), altitude (e.g., altimeter and/or GPS hardware might be employed), temperature (e.g., user temperature and/or environmental temperature), humidity, air pollution, barometric pressure, environmental topography, route (e.g., three-dimensional route) traveled, heart rate (e.g., heart rate meter hardware might be employed), respiration rate, heart electrophysiology (e.g., electrocardiogram hardware might be employed), blood oxygen saturation, number of steps taken and/or distance traveled (e.g., pedometer hardware might be employed), speed, elapsed time, and/or perspiration (e.g., skin conductance measuring hardware might be employed). It is noted that, in various embodiments, employed monitoring equipment might include one or more sensors. It is further noted that, in various embodiments, data so monitored and/or ascertained might, for instance, be stored (e.g., at a server) and/or mapped to video game parameters.

A number of determinations might, in various embodiments, be made. Such determinations might, for instance, be performed by user wireless nodes and/or other computers, and/or by other wireless nodes and/or other computers (e.g., by one or more servers).

For example, one or more determinations regarding the physiological state of a user performing a real-world fitness task might be made (step 203). Such determination might, for instance, involve determination of whether or not the user had reached a target heart rate, determination as to whether or not the user was experiencing acceptable blood oxygen saturation, and/or determination as to the extent to which the user was sweating.

As another example, one or more determinations regarding quality of real-world fitness task performance might be made (step 205). Such quality determination might, for instance, involve determining if a fitness task was performed in an acceptable manner and/or how well the fitness task was performed.

Determination of whether a fitness task was performed in an acceptable manner might be performed in a number of ways. For example GPS hardware and/or RFID interface hardware might be employed to determine that a user performing a fitness task performed the fitness task in a required location (e.g., in one of one or more acceptable fitness centers), that the user passed one or more required control points, and/or that the user performed the fitness task at and/or within close proximity of specified equipment (e.g., a specified exercise machine).

As an illustrative example, the geographical location of a user determined via GPS hardware and/or RFID tag interface hardware might be compared with a list of geographical locations corresponding to acceptable locations. Such functionality via RFID tag interface hardware might, for instance, involve communication with one or more RFID tags providing geographical location information. As another illustrative example, specified equipment might include RFID tags that provided identifiers. Identifiers read from such tags might, for instance, be compared with a list of identifiers corresponding to acceptable equipment. Such lists might, for example, be held in one or more stores accessible by a user's wireless node and/or other computer (e.g., one or more local and/or remote stores).

Determination of how well a real-world fitness task was performed might, for example, involve determination of the speed with which the fitness task was completed and/or determination of the number of errors committed in performing the fitness task.

As another example, one or more determinations regarding an environment in which a user performs a real-world fitness task might be made (step 207). Such determination might, for instance, involve determination of the ambient temperature of the environment, determination of the humidity of the environment, determination of the topography of the environment, determination of the ruggedness of the environment, and/or determination of the general distance of the environment above sea level. Determination of ruggedness might, for instance, take into account correlation between monitored altitudes and locations. To illustrate by way of example, an environment might be considered to be rugged in the case where small changes in geographical location yielded large changes in altitude.

Feedback regarding real-world fitness task performance might, in various embodiments, be provided to users (step 209). Such provided feedback might, for instance, include one or more scores and/or presentation regarding real-world fitness task progress. Such presentation might, in various embodiments, depict progress of a user performing a real-world fitness task relative to other users performing the real world fitness task. Such depiction might, in various embodiments, be within the game-world.

Feedback operations might, for example, be performed by one or more wireless nodes and/or other computers (e.g., servers, and/or wireless nodes and/or other computers of users), and/or might take into account various monitoring. It is noted that, in various embodiments, provided feedback might correspond to users and/or to teams. For example, a provided score might correspond to one or more users and/or to a team. It is further noted that, in various embodiments, real-time feedback might be provided.

It is further noted that, in various embodiments, the same stages and corresponding real-world fitness tasks might be presented to different teams such that, for example, teams could be compared against one another via feedback (e.g., scores). One or wireless nodes and/or other computers (e.g., one or more servers) might make available leaderboards showing, user and/or team performances. Such a leaderboard might, for example, show the performance of users with respect to other users, and/or the performance of teams with respect to other teams. A wireless node and/or other computer making available leaderboards might, for instance, make such leaderboards available for direct viewing by users (e.g., via a GUI and/or other interface provided by the node and/or other computer), and/or might make such leaderboards available for receipt by other wireless nodes and/or other computers. For example, a server might make leaderboards available for receipt by user wireless nodes and/or other computers, which in turn could provide leaderboard display to their users via GUIs and/or other interfaces.

In various embodiments, with completion of and/or during performance of a real-world fitness task, one or more scores (e.g., taking into account quality of real-world fitness task performance) might be presented. Such scores might, for instance, include scores for individual users (e.g., for users that had attempted the task) and/or team scores (e.g., for teams that had one or more users that attempted the task). Such scores might, for example, be presented via one or more GUIs and/or other interfaces provided by wireless nodes and/or other computers of users (e.g., of users that has attempted the task and/or that were members of a team that had one or more users that attempted the task).

As another example, with completion of and/or during performance of a real-world fitness task, display might be provided wherein graphical indicators corresponding to users that are performing and/or that have performed the real-world fitness task are positioned relative to one another, a goal corresponding to the task, and/or a route corresponding to the task. Such display might, for instance provide a game-world depiction and/or be presented via one or more GUIs and/or other interfaces provided by wireless nodes and/or other computers of users. Such display might, in various embodiments, take into account quality of real-world fitness task performance.

For example, in the case where a stage of a game requires that users reach a game-world landmark by performing a real-world fitness task of running and/or jogging, display might provide a graphical representation for each user performing the task and show the graphical representations as progressing along a game-world route terminating in the game-world landmark. A user viewing such display might, for instance, be able to determine how close each participating user was to the goal and/or how well each such user was competing relative to other such users.

In various embodiments, with completion of all stages of a game by a team, the team members might (e.g., via GUIs and/or other interfaces provided by their wireless nodes and/or other computers) have the ability to stop playing, to reformulate team memberships, and/or continue on to a new game.

It is noted that, in various embodiments, various of the above-discussed monitoring and feedback operations might involve communication among one or more wireless nodes and/or other computers of users, and/or other wireless nodes and/or other computers (e.g., one or more servers). Such communication might, for instance, involve RMI, JMS, SOAP, OBEX OPP, email, MMS, SMS, UMTS, GPRS, Bluetooth, wireless local area network, UWB, IrDA, wired network (e.g., Ethernet), and/or the Internet. In various embodiments, servers might be operated by service providers, and/or one or more user wireless nodes and/or other computers might act as servers.

Compensatory Operations

Compensatory operations might, in various embodiments, be performed. Such compensatory operations might, for example, be performed by one or more wireless nodes and/or other computers (e.g., servers, and/or wireless nodes and/or other computers of users).

Figure 3:
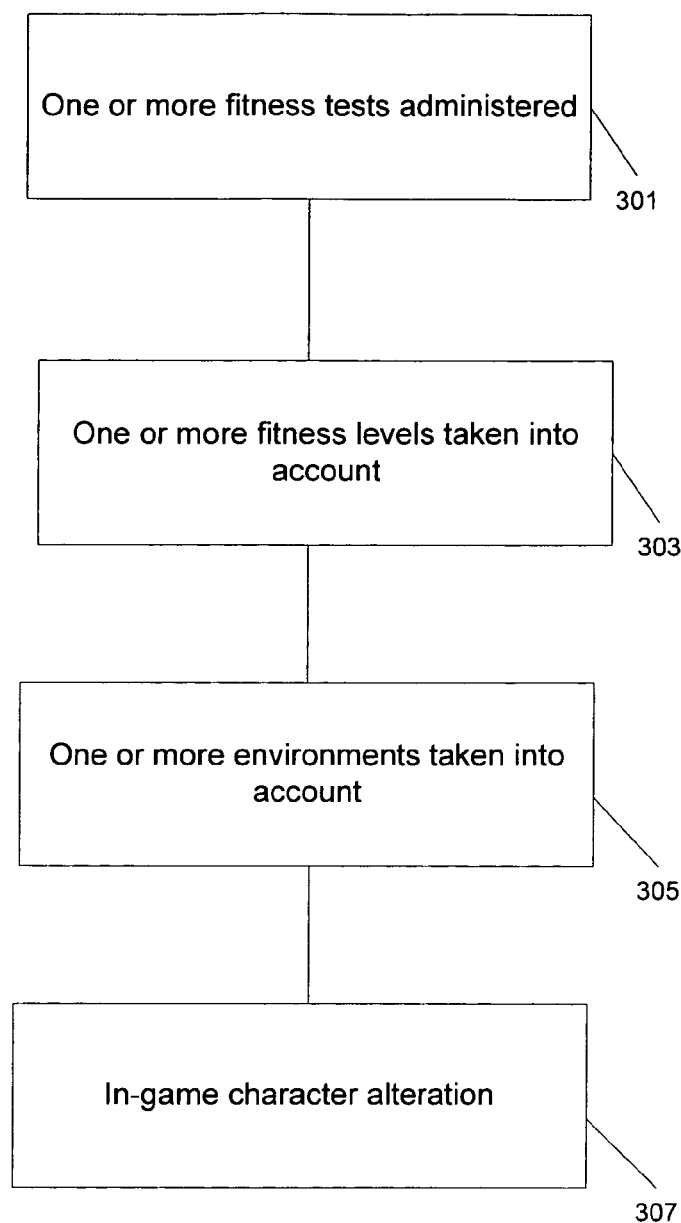
FIG. 3 shows exemplary steps involved in compensatory operations according to various embodiments of the present invention.

With respect to FIG. 3 it is noted that compensatory operations might, for example, take into account one or more fitness levels of users performing real-world fitness tasks (step 303) and/or the one or more environments in which real-world fitness tasks are performed (step 305). It is noted that, in various embodiments, fitness levels might include fitness levels corresponding to overall fitness and/or specific fitnesses. Such specific fitnesses might, for example, include cardiovascular fitness, strength fitness, aerobic fitness, and/or sport-specific fitness (e.g., fitness with respect to playing basketball). In various embodiments, compensation might be real-world fitness task specific (e.g., different compensation might be employed for different real-world fitness tasks). Compensatory operations might, in various embodiments, provide benefits including allowing for easier comparison between real-world fitness task performance by different users, and/or acting to prevent users that perform real-world fitness tasks in more challenging environments from being penalized for doing so.

Compensation might, for example, be employed in providing feedback (e.g., of the sort discussed above) to users. For instance, compensation might be employed in the provision of scores, and/or in the provision of display wherein graphical indicators corresponding to users are positioned relative to one another, a goal, and/or a route. Such compensation might, in various embodiments, be employed as an alternative to and/or in addition to taking into account quality of real-world fitness task performance. Such functionality might be implemented in a number of ways.

For example, provision of a score regarding a user's performance of a real-world fitness task might take into account one or more fitness levels of the user such that performance of the task in a certain manner would yield a higher score in the case where one or more lower fitness levels were associated with the user and/or would yield a lower score in the case where one or more higher fitness levels were associated with the user. As an illustrative example, in the case where overall fitness was to be taken into account in scoring and the real-world fitness task was to run a certain distance, in the case where two users ran the distance in the same amount of time the user associated with the lower overall fitness level might receive the higher score.

As another example, provision of display wherein graphical indicators corresponding to users are positioned relative to one another, a goal, and/or a route might take into account one or more fitness levels of a user such that performance of the task in a certain manner would result in greater progress being depicted by the display in the case where one or more lower fitness levels were associated with the user and/or would result in lesser progress being depicted by the display in the case where one or more higher fitness levels were associated with the user. As an illustrative example, in the case where overall fitness level was to be taken into account in display and the real-world fitness task involved running, in the case where two users performing the real-world fitness task each traveled the same real-world distance within a certain elapsed time, the user associated with the lower overall fitness level might be depicted as having gone further.

It is noted that, in various embodiments, in the case where one or more higher fitness levels came to be associated with a user (e.g., by way of the user becoming more physically fit), the user might need to perform a real-world fitness task more effectively in order to receive the same score and/or experience depiction of as much progress as she did when one or more lower fitness levels were associated with her.

It is further noted that, in various embodiments, in the case where multiple users perform a certain sort of real-world fitness task (e.g., one relating to a specific sport) equally well, but some of the users tend to be better at that sort of real-world fitness task and others of the users tends to be worse at that sort of real world fitness task, the users that tend to be worse at that sort of real-world fitness task might receive more positive scores and/or experience more positive depictions. As an illustrative example, in the case where a user that tends to swim well and a user that tends to not swim well each perform a real-world fitness task involving swimming equally well, the user that tends to not swim well might receive the more positive score and/or experience the more positive depiction. A user tending to be better or worse at a certain sort of real-world fitness task might, for instance, be indicated via one or more specific fitnesses.

As yet another example, provision of a score regarding a user's performance of a real-world fitness task might take into account one or more environments in which the real-world fitness task is performed such that performance of the task in a certain manner would yield a higher score in the case where the user performed the task in one or more environments considered to be more challenging and/or would yield a lower score in the case where the user performed the task in one or more environments considered to be less challenging. As an illustrative example, in the case where the real world fitness task was to run a certain distance, if two users ran the distance in the same amount of time the user that performed the task in the more challenging environment might receive the higher score.

As a further example, provision of display wherein graphical indicators corresponding to users are positioned relative to one another, a goal, and/or a route might take into account one or more environments in which the real-world fitness task is performed such that performance of the task in a certain manner would result in greater progress being depicted by the display in the case where task performance was in one or more environments considered to be more challenging and/or would result in lesser progress being depicted by the display in the case where task performance was in one or more environments considered to be less challenging. As an illustrative example, in the case where the real-world fitness task involved running, in the case where two users performing the real-world fitness task each traveled the same real-world distance within a certain elapsed time, the user performing the task in one or more environments considered to be more challenging might be depicted as having gone further.

It is noted that, in various embodiments, provision of display wherein graphical indicators corresponding to users are positioned relative to one another, a goal, and/or a route might be performed under circumstances where users performing a real-world are performing the task at the same time and/or where users performing the real-world fitness task are performing the task at different times. In the case where not all users performing the task do so at the same time, one or more operations might, in various embodiments, be implemented.

For example, display might be provided for a particular user performing a real-world fitness task such that display shows a graphical indication corresponding to the user that is positioned relative to graphical representations corresponding to users performing the task at the same time as the user and/or users that had performed the task prior to the user. Presentation regarding users that had already performed the task might, for instance, make use of data recorded at the time those users performed the task. In various embodiments, presentation might graphically depict which graphical indicators corresponded to users presently performing and which corresponded to users that had previously performed. For example, graphical indications corresponding to users that had previously performed might be graphically transparent to a certain degree.

It is noted that, in various embodiments, in the case where not all users perform a real-world fitness task at the same time, users might, for example, be informed (e.g., via GUIs and/or other interfaces of their wireless nodes and/or other computers) that they may not know their game-world performance (e.g., distance traveled in the game-world and/or score awarded) until all users had performed the task. As another example, such a user might be informed (e.g., by a GUI and/or other interface of her wireless node and/or other computer) once she had reached a certain performance threshold in the real-world (e.g., once she had traveled a certain distance). Such a performance threshold might, in various embodiments, be chosen by participating users and/or by one or more wireless nodes and/or other computers.

In various embodiments, the user might, alternately or additionally, be so informed once she had reached the performance threshold plus a certain tolerance amount. Having the user perform to beyond the threshold by such a tolerance amount might, in various embodiments, allow for collection of additional data useful, for instance, in computing game-world performance for users after completion of real-world fitness task performance by all participating users (e.g., in the case where additional data can be employed to break what would have otherwise been a tie). Computation after completion of real-world fitness task performance by all participating users might, for example, be performed by one or more user wireless nodes and/or other computers, and/or other wireless nodes and/or other computers (e.g., one or more servers). A participating user might, for instance, learn of the results of such computation via a GUI and/or other interface provided by her wireless node and/or other computer.

Determination of the extent to which various factors (e.g., fitness levels and/or environments) should be taken into account in compensation might be performed in a number of ways. For example, a data collection period (e.g., during game development) might be employed wherein users having various associated fitness levels (e.g., users having differing associated overall fitness levels) perform various real-world fitness tasks under various environmental conditions. Data (e.g., of the sort discussed above) might be collected during task performance. The collected data might, for instance, be subjected to data analysis (e.g., statistical analysis and/or data mining), expert analysis (e.g., physician and/or fitness expert analysis), and/or modeling (e.g., physics-based modeling). Such modeling might, for example, consider differences in three-dimensional routes, topography, and/or ruggedness from the point of view of, for instance, how such differences might affect required energy exertion.

For example, in various embodiments various environmental factors might be taken into account in determining how challenging an environment is. Such factors might, for instance, include topography, ruggedness, general distance above sea level, humidity, and/or ambient temperature. As another example, data analysis (e.g., statistical analysis and/or data mining) and/or expert opinion might be employed. Such experts might, for instance, include physicians and/or fitness experts.

It is noted that, in various embodiments, compensation might take into account both one or more fitness levels and one or more environments. Such functionality might, for instance, be implemented in a manner analogous to that discussed above. It is noted that, in various embodiments, such functionality might involve cross-comparison between fitness level impact on real-world fitness task performance and environmental impact on real-world fitness task performance.

As an illustrative example, suppose that score, taking into account both environment and overall fitness level, was to be provided for a situation in which two users performed a real-world fitness task of running a certain distance, and both users ran the distance in the same amount of time. Suppose further that the environment of the first user was more challenging than the environment of the second user, but that the second user was associated with a lower overall fitness level than the first user. Determination of which user was to receive the higher score might, for instance, involve cross-comparison of the sort discussed above.

Cross-comparison functionality might be implemented in a number of ways. For example, data analysis (e.g., of the sort discussed above) and/or expert opinion might be employed in determining what weight should be accorded to fitness level and what weight should be accorded to environment under various circumstances. Such experts might, for instance, include those of the sort discussed above.

It is noted that, in various embodiments, cross-comparison functionality might be implemented that allowed for cross-comparison among users competing in different real-world fitness tasks. In various embodiments, strenuousness of tasks might be taken into account. Cross-comparison functionality regarding performance of different real-world fitness tasks might, in various embodiments, be implemented in a manner analogous to that discussed above (e.g., data analysis and/or expert opinion might be employed).

It is noted that, in various embodiments, cross-comparison functionality regarding performance of different real-world fitness tasks might, for example, involve users being asked (e.g., with initial signup and/or before the start of a game) to rate their skills (e.g., on a scale of 1 to 5 where "5" is the best) with regard to different real-world fitness tasks. For instance, a user might be asked to rate her skills on a scale of 1 to 5 with regard to running, bicycling, swimming, and/or other real-world fitness tasks to be involved in one or more games.

As another example, users might (e.g., with initial signup and/or before the start of a game) be asked to perform various real-world fitness tasks. Fitness task performance might, for instance, be monitored and/or rated (e.g., in a manner analogous to that discussed herein). A rating (e.g., on a scale of 1 to 5 where "5" is the best) might, for instance, be given with regard to each performed task.

Scaled ratings might, in various embodiments, be such that in the case where two users performed a real-world fitness task equally well, but one had a rating of "1" for that task and the other had a rating of "4" for that task, that the user having the rating of "1" would receive greater reward (e.g., a higher score) than the user having a rating of "4".

It is noted that, in various embodiments, a rating for a particular real-world fitness task might be upgraded as a user performed more of that task. To illustrate by way of example, a user that was initially a poor runner might start with a rating of "2" for running on a scale of 1 to 5 where "5" was the best. As the user performed more running tasks, her rating might rise to "4". Consequently, the user might, in various embodiments, be rewarded by a decreasing amount as she performed more and more running tasks and her skills developed.

Cross-comparison functionality regarding performance of different real-world fitness tasks might, for example, allow for a game stage wherein a landmark is to be reached in the game-world by way of a first user performing a real-world fitness task of running and a second user performing a real-world fitness task of swimming such that the two users can be directly set against one another via feedback of the sort discussed above (e.g., scoring, and/or display wherein graphical indicators corresponding to users are positioned relative to one another, a goal, and/or a route). It is noted that, in various embodiments, users might be able to select (e.g., via GUIs and/or other interfaces of their wireless nodes and/or other computers) the real-world fitness tasks that they wanted to perform with respect to a game stage, with cross-comparison functionality corresponding to differing real-world fitness tasks perhaps being employed.

One or more user fitness levels might, in various embodiments, be obtained through administration of one or more fitness tests (step 301). Fitness tests might be administered under a variety of circumstances. For example, one or more fitness tests might be administered to a user in conjunction with initial signup of that user (e.g., in conjunction with initial signup of the user to participate in video games wherein real-world fitness tasks are performed in the context of the game. As another example, one or more fitness tests might be administered to a user before the start of a game. Accordingly, for instance, one or more fitness tests might be administered before the start of certain games (e.g., before the start of each game or before the start of each third game). As yet another example, one or more fitness tests might be administered to a user periodically (e.g., every certain number of hours, days, weeks and/or months). Values corresponding to how frequently fitness tests are administered to users might, for instance, be set by physicians and/or fitness experts.

Various types of fitness tests might, in various embodiments, be administered. Administered fitness tests might, for example, include Cooper Tests, step tests, cardiac stress tests, maximal oxygen uptake tests (e.g., involving blood gas analysis), and/or tests predicting maximal oxygen uptake. Such a test predicting maximal oxygen uptake might, in various embodiments, consider pulse (e.g., pulse and/or pulse variability at rest), age, gender, height, weight, and/or physical activity level. It is noted that, in various embodiments, such a test predicting maximal oxygen uptake might yield a score comparable to maximal oxygen uptake. In various embodiments, fitness tests might be administered in one or more controlled environments.

Administration of a fitness test might, for instance, involve the use of monitoring (e.g., of the sort discussed above) and/or communication with equipment (e.g., exercise equipment). For example, monitoring of elapsed time and/or distance traveled might, perhaps as discussed above, be performed in connection with Cooper Test administration. Communication with equipment might, for instance, be performed in the case where a test predicting maximal oxygen uptake (e.g., via a piece of exercise equipment and/or a pulse meter) and/or cardiac stress test (e.g., via a treadmill and heart monitoring equipment) is administered. Equipment might, for example, communicate with a user's wireless node and/or other computer (e.g., to provide fitness test results). Such communication might, for instance, be performed in a manner analogous to that discussed above (e.g., Bluetooth, WiFi, OBEX OPP, and/or SOAP might be employed). A user to whom a fitness task is administered might, in various embodiments, receive one or more corresponding instructions and/or indications (e.g., by way of a GUI and/or other interface provided by her wireless node and/or other computer).

It is noted that, in various embodiments, fitness test administration might involve communication between one or more wireless nodes and/or other computers. For instance, fitness test administration to a user might involve that user's wireless node and/or other computer providing data corresponding to the test (e.g., test results and/or data corresponding to monitoring) to one or more other wireless nodes and/or other computers (e.g., one or more servers).

It is further noted that, in various embodiments, various data to be employed in fitness test administration might be requested from users (e.g., via GUIs and/or other interfaces of their wireless nodes and/or other computers) and/or be recorded from users. Such data might, for instance, include age, gender, weight, target heart rate range, muscle strength, stamina, and/or special skills (e.g., skills in swimming, running, and/or cycling). Such data might, for example, be requested and/or recorded from users in conjunction with initial signup and/or before fitness test administration.

In various embodiments, certain of such data (e.g., age and gender) might be requested from users, certain of such data might be recorded from users, and/or certain of such data (e.g., weight and/or muscle strength) might be either requested from users and/or measured. For instance, a user's weight might be requested from the user and/or might be recorded by having the user stand on a scale that communicates the user's weight to her wireless node and/or other computer. The user's wireless node and/or other computer might, in turn, pass the information to another node and/or other computer (e.g., a server).

In various embodiments of the present inventions, in-game characters corresponding to users might be altered under certain circumstances (step 307). For example, the in-game character corresponding to a user might be altered to look stronger in the case where the user performed extra real-world fitness tasks, where one or more fitness levels associated with the user increased, and/or where the user received increasing scores corresponding to the performance of real-world fitness tasks. As another example, the in-game character corresponding to a user might be altered to look weaker in the case where the user performed no extra real-world fitness tasks, where one or more fitness levels associated with the user decreased, and/or where the user received decreasing scores corresponding to the performance of real-world fitness tasks.

As yet another example, the in-game character corresponding to a user might be altered in view of specific fitness levels of that user and/or the extent to which that user performed specific real-world fitness tasks. As an illustrative example, in the case where a user was a poor runner and/or cyclist, her in-game character might have small and/or weak looking legs. As the user performed more running and/or cycling real-world fitness tasks, the in-game character's legs might appear stronger and/or larger.

It is further noted that, in various embodiments, the appearance of a user's in-game character might reflect whether or not the user took a balanced approach to fitness. As an illustrative example, in the case where a user performed many real-world fitness tasks involving her legs (e.g., running and/or cycling) but few involving her upper body (e.g., tasks involving weights), her in-game character might look unbalanced, having strong and/or large looking legs but a small and/or weak looking upper body.

It is noted that, in various embodiments, various of the above-discussed compensatory operations might involve communication among one or more wireless nodes and/or other computers of users, and/or other wireless nodes and/or other computers (e.g., one or more servers). Such communication might, for instance, involve RMI, JMS, SOAP, OBEX OPP, email, MMS, SMS, UMTS, GPRS, Bluetooth, wireless local area network, UWB, IrDA, wired network (e.g., Ethernet), and/or the Internet. In various embodiments, servers might be operated by service providers, and/or one or more user wireless nodes and/or other computers might act as servers.

Hardware and Software

Various operations and/or the like described herein may, in various embodiments, be executed by and/or with the help of computers. Further, for example, devices described herein may be and/or may incorporate computers. The phrases "computer", "general purpose computer", and the like, as used herein, refer but are not limited to a smart card, a media device, a personal computer, an engineering workstation, a PC, a Macintosh, a PDA, a portable computer, a computerized watch, a wired or wireless terminal, phone, communication device, node, and/or the like, a server, a network access point, a network multicast point, a network device, a set-top box, a personal video recorder (PVR), a game console, a portable game device, a portable audio device, a portable media device, a portable video device, a television, a digital camera, a digital camcorder, a Global Positioning System (GPS) receiver, a wireless personal sever, or the like, or any combination thereof, perhaps running an operating system such as OS X, Linux, Darwin, Windows CE, Windows XP, Windows Server 2003, Palm OS, Symbian OS, or the like, perhaps employing the Series 40 Platform, Series 60 Platform, Series 80 Platform, and/or Series 90 Platform, and perhaps having support for Java and/or Net.

Figure 4:
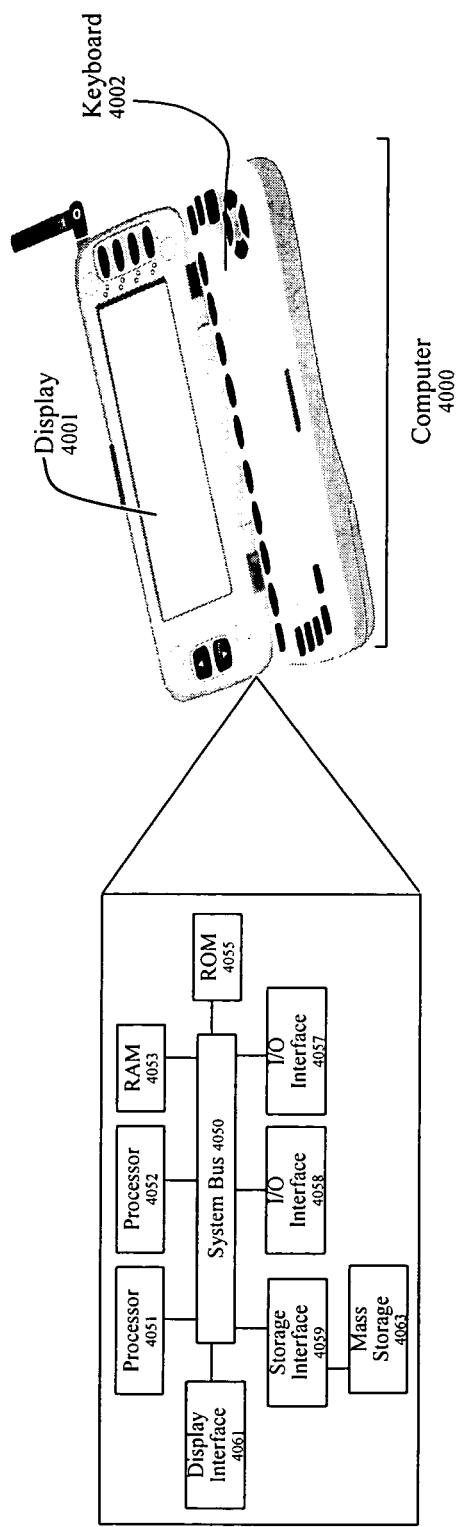
FIG. 4 shows an exemplary computer.

The phrases "general purpose computer", "computer", and the like also refer, but are not limited to, one or more processors operatively connected to one or more memory or storage units, wherein the memory or storage may contain data, algorithms, and/or program code, and the processor or processors may execute the program code and/or manipulate the program code, data, and/or algorithms. Shown in FIG. 4 is an exemplary computer employable in various embodiments of the present invention. Exemplary computer 4000 includes system bus 4050 which operatively connects two processors 4051 and 4052, random access memory 4053, read-only memory 4055, input output (I/O) interfaces 4057 and 4058, storage interface 4059, and display interface 4061. Storage interface 4059 in turn connects to mass storage 4063. Each of I/O interfaces 10057 and 10058 may, for example, be an Ethernet, IEEE 1394, IEEE 1394b, IEEE 802.11a, IEEE 802.11b, IEEE 802.11g, IEEE 802.11i, IEEE 802.11e, IEEE 802.11n, IEEE 802.15a, IEEE 802.16a, IEEE 802.16d, IEEE 802.16e, IEEE 802.16x, IEEE 802.20, IEEE 802.15.3, Zig-Bee (e.g., IEEE 802.15.4), Bluetooth, Ultra Wide Band (UWB), Wireless Universal Serial Bus (WUSB), wireless Firewire, terrestrial digital video broadcast (DVB-T), satellite digital video broadcast (DVB-S), Advanced Television Systems Committee (ATSC), Integrated Services Digital Broadcasting (ISDB), Digital Multimedia Broadcast-Terrestrial (DMB-T), MediaFLO (Forward Link Only), Terrestrial Digital Multimedia Broadcasting (T-DMB), Digital Audio Broadcast (DAB), Digital Radio Mondiale (DRM), General Packet Radio Service (GPRS), Universal Mobile Telecommunications Service (UMTS), Global System for Mobile Communications (GSM), Code Division Multiple Access 2000 (CDMA2000), DVB-H (Digital Video Broadcasting: Handhelds), IrDA (Infrared Data Association), and/or other interface.

Mass storage 4063 may be a hard drive, optical drive, a memory chip, or the like. Processors 4051 and 4052 may each be a commonly known processor such as an IBM or Freescale PowerPC, an AMD Athlon, an AMD Opteron, an Intel ARM, an Intel XScale, a Transmeta Crusoe, a Transmeta Efficeon, an Intel Xenon, an Intel Itanium, an Intel Pentium, an Intel Core, or an IBM, Toshiba, or Sony Cell processor. Computer 4000 as shown in this example also includes a touch screen 4001 and a keyboard 4002. In various embodiments, a mouse, keypad, and/or interface might alternately or additionally be employed. Computer 4000 may additionally include or be attached to card readers, DVD drives, floppy disk drives, hard drives, memory cards, ROM, and/or the like whereby media containing program code (e.g., for performing various operations and/or the like described herein) may be inserted for the purpose of loading the code onto the computer.

In accordance with various embodiments of the present invention, a computer may run one or more software modules designed to perform one or more of the above-described operations. Such modules might, for example, be programmed using languages such as Java, Objective C, C, C#, C++, Perl, Python, and/or Comega according to methods known in the art. Corresponding program code might be placed on media such as, for example, DVD, CD-ROM, memory card, and/or floppy disk. It is noted that any described division of operations among particular software modules is for purposes of illustration, and that alternate divisions of operation may be employed. Accordingly, any operations discussed as being performed by one software module might instead be performed by a plurality of software modules. Similarly, any operations discussed as being performed by a plurality of modules might instead be performed by a single module. It is noted that operations disclosed as being performed by a particular computer might instead be performed by a plurality of computers. It is further noted that, in various embodiments, peer-to-peer and/or grid computing techniques may be employed. It is additionally noted that, in various embodiments, remote communication among software modules may occur. Such remote communication might, for example, involve Simple Object Access Protocol (SOAP), Java Messaging Service (JMS), Remote Method Invocation (RMI), Remote Procedure Call (RPC), sockets, and/or pipes.

Figure 5:
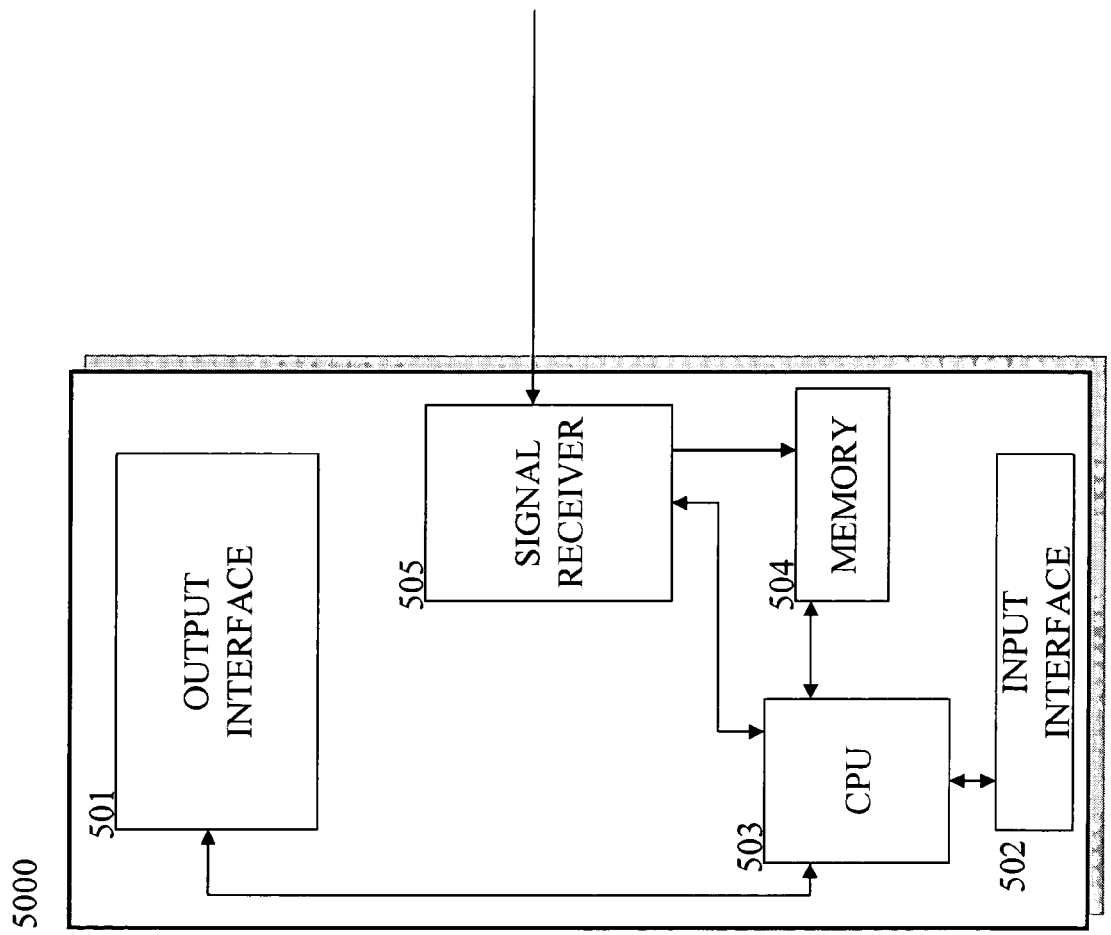
FIG. 5 shows a further exemplary computer.

Shown in FIG. 5 is a block diagram of a terminal, an exemplary computer employable in various embodiments of the present invention. In the following, corresponding reference signs are applied to corresponding parts. Exemplary terminal 5000 of FIG. 5 comprises a processing unit CPU 503, a signal receiver 505, and a user interface (501, 502). Signal receiver 505 may, for example, be a single-carrier or multi-carrier receiver. Signal receiver 505 and the user interface (501, 502) are coupled with the processing unit CPU 503. One or more direct memory access (DMA) channels may exist between multi-carrier signal terminal part 505 and memory 504. The user interface (501, 502) comprises a display and a keyboard to enable a user to use the terminal 5000. In addition, the user interface (501, 502) comprises a microphone and a speaker for receiving and producing audio signals. The user interface (501, 502) may also comprise voice recognition (not shown).

The processing unit CPU 503 comprises a microprocessor (not shown), memory 504 and possibly software. The software can be stored in the memory 504. The microprocessor controls, on the basis of the software, the operation of the terminal 5000, such as receiving of a data stream, tolerance of the impulse burst noise in data reception, displaying output in the user interface and the reading of inputs received from the user interface. The hardware contains circuitry for detecting signal, circuitry for demodulation, circuitry for detecting impulse, circuitry for blanking those samples of the symbol where significant amount of impulse noise is present, circuitry for calculating estimates, and circuitry for performing the corrections of the corrupted data.

Still referring to FIG. 5, alternatively, middleware or software implementation can be applied. The terminal 5000 can, for instance, be a hand-held device which a user can comfortably carry. The terminal 5000 can, for example, be a cellular mobile phone which comprises the multi-carrier signal terminal part 505 for receiving multicast transmission streams. Therefore, the terminal 5000 may possibly interact with the service providers.

It is noted that various operations and/or the like described herein may, in various embodiments, be implemented in hardware (e.g., via one or more integrated circuits). For instance, in various embodiments various operations and/or the like described herein may be performed by specialized hardware, and/or otherwise not by one or more general purpose processors. One or more chips and/or chipsets might, in various embodiments, be employed. In various embodiments, one or more Application-Specific Integrated Circuits (ASICs) may be employed.

RAMIFICATIONS AND SCOPE

Although the description above contains many specifics, these are merely provided to illustrate the invention and should not be construed as limitations of the invention's scope. Thus it will be apparent to those skilled in the art that various modifications and variations can be made in the system and processes of the present invention without departing from the spirit or scope of the invention.

In addition, the embodiments, features, methods, systems, and details of the invention that are described above in the application may be combined separately or in any combination to create or describe new embodiments of the invention.

What is claimed is:

1. An apparatus, comprising:
at least one processor; and
at least one memory including computer program code for one or more programs,
the at least one memory and the computer program code configured to, with the at least one processor, cause the apparatus to perform at least the following,
specify via a multiplayer video game a real-world fitness task to be performed;
receive monitored information regarding performance of the fitness task; and
determine to provide indication regarding the performance of the fitness task, wherein the indication takes into account one or more factors regarding a real-world environment associated with a user, wherein the factors relate to topography of the environment, a climatic condition of the environment, or a combination thereof, during the fitness task, and
wherein completion of the fitness task results in advancement in the video game.

2. The apparatus of claim 1, wherein the indication comprises one or more scores regarding the performance of the fitness task.

3. The apparatus of claim 1, wherein the indication comprises game-world representation of progress relative to one or more users performing the fitness task.

4. The apparatus of claim 1, wherein the one or more factors include topography of the environment in which the fitness task is performed.

5. The apparatus of claim 1, wherein the one or more factors include one or more climatic conditions of the environment in which the fitness task is performed.

6. The apparatus of claim 1, wherein the apparatus is further caused to receive results of one or more fitness tests.

7. The apparatus of claim 1, wherein one or more sensors are employed in monitoring fitness task performance.

8. The apparatus of claim 1, wherein the fitness task is performed by multiple members of a team.

9. The apparatus of claim 1, wherein the apparatus is further caused to: determine acceptability of the performance of the fitness task.

10. The apparatus of claim 1, wherein the apparatus is further caused to: offer team formation functionality.

11. An apparatus, comprising:
a memory having program code stored therein; and
a processor disposed in communication with the memory for carrying out instructions in accordance with the stored program code;
wherein the program code, when executed by the processor, causes the processor to perform:
specifying via a multiplayer video game a real-world fitness task to be performed;
receiving monitored information regarding performance of the fitness task; and
determining to provide adjusted indication regarding the performance of the fitness task during the fitness task, wherein the adjustment takes into account one or more fitness levels and a real-world environment associated with a user, including topography of the environment, climatic conditions of the environment, or a combination thereof, and
wherein completion of the fitness task results in advancement in the video game.

12. The apparatus of claim 11, wherein the indication comprises one or more scores regarding the performance of the fitness task.

13. The apparatus of claim 11, wherein the indication comprises game-world representation of progress relative to one or more users performing the fitness task.

14. The apparatus of claim 11, wherein the one or more fitness levels include an overall fitness.

15. The apparatus of claim 11, wherein the one or more fitness levels include one or more specific fitnesses.

16. The apparatus of claim 11, wherein the processor further performs receiving results of one or more fitness tests.

17. The apparatus of claim 11, wherein one or more sensors are employed in monitoring fitness task performance.

18. The apparatus of claim 11, wherein the fitness task is performed by multiple members of a team.

19. The apparatus of claim 11, wherein the processor further performs determining acceptability of the performance of the fitness task.

20. The apparatus of claim 11, wherein the processor further performs providing team formation functionality.

21. An apparatus, comprising:
a memory having program code stored therein; and
a processor disposed in communication with the memory for carrying out instructions in accordance with the stored program code;
wherein the program code, when executed by the processor, causes the processor to perform:
specifying via a multiplayer video game a real-world fitness task to be performed;
receiving input from a plurality of users relating to voting for one of the users to perform the fitness task;
receiving monitored information regarding performance of the fitness task; and
determining to provide indication regarding the performance of the fitness task, wherein the indication takes into account one or more factors regarding a real-world environment associated with the one user, wherein the factors relate to topography of the environment, a climatic condition of the environment, or a combination thereof, during the fitness task, and wherein completion of the fitness task results in advancement in the video game.

22. An apparatus, comprising:
at least one processor; and
at least one memory including computer program code for one or more programs,
the at least one memory and the computer program code configured to, with the at least one processor, cause the apparatus to perform at least the following,
specify via a multiplayer video game a real-world fitness task to be performed;
receive monitored information regarding performance of the fitness task; and
determine to provide adjusted indication regarding the performance of the fitness task the fitness task, wherein the adjustment takes into account one or more fitness levels of the user and a real-world environment associated with a user, including topography of the environment, climatic conditions of the environment, or a combination thereof, and
wherein completion of the fitness task results in advancement in the video game, and an in-game character corresponding to the user is altered based on the one or more fitness levels.

23. A method, comprising:
determining, at a processor, to specify to a user, via a multiplayer video game, a real-world fitness task to be performed;
receiving monitored information regarding performance of the fitness task by the user; and
determining to provide a user indication regarding the performance of the fitness task based on the monitored information, wherein the indication takes into account one or more factors regarding a real-world environment associated with the user, wherein the factors relate to topography of the environment, a climatic condition of the environment, or a combination thereof, during the fitness task, and
wherein completion of the fitness task results in advancement in the video game.

24. A method, comprising:
determining, at a processor, to specify to a user, via a multiplayer video game, a real-world fitness task to be performed;
receiving monitored information regarding performance of the fitness task by the user; and
determining to provide to the user adjusted indication regarding the performance of the fitness task based on the monitored information, wherein the adjustment takes into account one or more fitness levels of the user and one or more real-world environment factors associated with the user, wherein the factors relate to topography of the environment, a climatic condition of the environment, or a combination thereof, during the fitness task, and wherein completion of the fitness task results in advancement in the video game.

25. A non-transitory computer-readable storage medium carrying one or more sequences of one or more instructions which, when executed by one or more processors, cause an apparatus to at least perform the following steps:
specifying to a user, via a multiplayer video game, a real-world fitness task to be performed;
receiving monitored information regarding performance of the fitness task by the user; and
determining to provide to the user indication regarding the performance of the fitness task, wherein the indication takes into account one or more factors regarding a real-world environment associated with the user, wherein the factors relate to topography of the environment, climatic conditions of the environment, or a combination thereof, during the fitness task, and
wherein completion of the fitness task results in advancement in the video game.

26. A non-transitory computer-readable storage medium carrying one or more sequences of one or more instructions which, when executed by one or more processors, cause an apparatus to at least perform the following steps:
specifying to a user, via a multiplayer video game, a real-world fitness task to be performed;
receiving monitored information regarding performance of the fitness task by the user; and
determining to provide to the user adjusted indication regarding the performance of the fitness task, wherein the adjustment takes into account one or more fitness levels of the user and one or more real-world environment factors associated with the user, wherein the factors include a topography of the environment, a climatic condition of the environment, or a combination thereof, during the fitness task, and wherein completion of the fitness task results in advancement in the video game.

27. A method of claim 23, further comprising:
determining a score based on the fitness task, the topography, the climatic conditions, or a combination thereof, wherein the indication includes the score.

28. A method of claim 23, further comprising:
determining a score based on the fitness task, the topography, the climatic conditions, ruggedness of the environment, altitude of the environment, or a combination thereof,
wherein the indication includes the score.

29. A method of claim 28, further comprising:
determining to alter an appearance of an in-game character according to the score.

* * * * *